US012752100B2

(12) United States Patent
Frischke

(10) Patent No.: US 12,752,100 B2
(45) Date of Patent: Oct. 6, 2026

(54) CONNECTOR UNIT, CONTROL UNIT AND CONTROL SYSTEM

(71) Applicant: Berlin Heart GmbH, Berlin (DE)

(72) Inventor: Michael Frischke, Rangsdorf (DE)

(73) Assignee: Berlin Heart GmbH, Berlin (DE)

( * ) Notice: Subject to any disclaimer, the term of this patent is extended or adjusted under 35 U.S.C. 154(b) by 455 days.

(21) Appl. No.: 18/327,937

(22) Filed: Jun. 2, 2023

(65) Prior Publication Data

US 2023/0310838 A1 Oct. 5, 2023

Related U.S. Application Data

(63) Continuation of application No. PCT/EP2021/084201, filed on Dec. 3, 2021.

(30) Foreign Application Priority Data

Dec. 4, 2020 (EP) .................................... 20211949

(51) Int. Cl.
*A61M 60/871* (2021.01)
*A61M 60/126* (2021.01)
*H01R 13/52* (2006.01)

(52) U.S. Cl.
CPC ........ *A61M 60/871* (2021.01); *A61M 60/126* (2021.01); *H01R 13/521* (2013.01); *H01R 13/5224* (2013.01); *H01R 2201/12* (2013.01)

(58) Field of Classification Search
CPC . A61M 60/871; A61M 60/126; H01R 13/521; H01R 13/5224; H01R 2201/12
See application file for complete search history.

(56) References Cited

U.S. PATENT DOCUMENTS

2012/0022452 A1 1/2012 Welsch et al.
2016/0089483 A1* 3/2016 Chen .................. A61M 60/873 600/17

(Continued)

FOREIGN PATENT DOCUMENTS

CN 102046225 A 5/2011
CN 109641094 A 4/2019

(Continued)

OTHER PUBLICATIONS

International Search Report and Written Opinion of the International Search Authority mailed May 23, 2022 in International Application No. PCT/EP2021/084201 (English and German languages) (11 pp.).

(Continued)

*Primary Examiner* — Lindsey G Wehrheim
(74) *Attorney, Agent, or Firm* — Crowell & Moring LLP

(57) ABSTRACT

A connector unit for a control unit is configured to control an implantable blood pump. The connector unit includes a supply interface designed for connecting the connector unit to a power supply, a data interface designed for connecting the connector unit to a data processing unit, and a control interface designed for connecting the connector unit to an integrated interface of the control unit. A supply connection of the control unit to the power supply and a data connection of the control unit to the data processing unit can be established at the same time by means of the connector unit. The application furthermore relates to a control unit for controlling an implantable blood pump and to a control system for an implantable blood pump.

13 Claims, 2 Drawing Sheets

(56) References Cited

U.S. PATENT DOCUMENTS

| | | | |
|---|---|---|---|
| 2018/0256798 A1 | 9/2018 | Botterbusch et al. | |
| 2019/0134286 A1* | 5/2019 | Johnson .............. | A61M 60/592 |

FOREIGN PATENT DOCUMENTS

| | | |
|---|---|---|
| CN | 110636873 A | 12/2019 |
| CN | 111315423 A | 6/2020 |

OTHER PUBLICATIONS

First Office Action for China Patent Application No. 202180080677.9 dated Jul. 19, 2025 (With English Translation) (14 pages total).

* cited by examiner

CONNECTOR UNIT, CONTROL UNIT AND CONTROL SYSTEM

PRIORITY

This application claims priority as a Continuation of PCT/EP2021/084201, filed on Dec. 3, 2021, entitled "CONNECTOR UNIT, CONTROL UNIT AND CONTROL SYSTEM", published as WO 2022/117832 A1, which claims priority to European Patent Application No. 20 211 949.1 filed on Dec. 4, 2020, entitled "CONNECTOR UNIT, CONTROL UNIT AND CONTROL SYSTEM". The entire disclosures of the above applications are incorporated herein by reference.

TECHNICAL FIELD

The application relates to a connector unit for a control unit/system configured to control an implantable blood pump.

BACKGROUND

Control systems for implantable blood pumps and components of such control systems, in particular control units and connector units, are known from the prior art. In control systems in accordance with the prior art, the control unit is frequently connected to an external rechargeable battery for a voltage supply by means of a cable connection.

Such a control system may need improvement with respect to its compact size, its robustness, its handling, and its service life.

SUMMARY

It is furthermore advantageous during surgery for implantation of a blood pump to provide the control unit within a sterile operating area for connection to the blood pump so that the control system and its components should be adapted for such a use.

The control unit should accordingly be able to be supplied with voltage and be externally controllable and/or programmable in the operating area. However, no non-sterile objects (for instance cable connections or other connector units, external data processing units, or external rechargeable batteries, where not sterile or not sterilizable in a practical manner) may be brought into the sterile operating area.

Safe operation, in particular electrical safety, is furthermore of great importance in medical devices.

It is the underlying object of the present application against the background of the prior art to propose a connector unit, a control unit, and a control system such that a power supply and/or a control of the control unit can take place in the simplest possible manner within a sterile operating area, with the connector unit, the control unit, and the control system being as compact, robust, simple to handle, and long-lasting as possible and enabling safe operation.

A connector unit in accordance with claim 1, a control unit in accordance with claim 7, and a control system in accordance with claim 13 are proposed to achieve the object. Advantageous embodiments and further developments result from the features in accordance with the dependent claims.

The proposed connector unit for a control unit configured to control an implantable blood pump comprises:

- a supply interface configured to connect the connector unit to a power supply;

- a data interface configured to connect the connector unit to a data processing unit; and
- a control interface configured to connect the connector unit to an integrated interface of the control unit so that a supply connection of the control unit to the power supply and a data connection of the control unit to the data processing unit can simultaneously be established by means of the connector unit.

An interface is here in particular understood as an independently connectable or connected connection point for an electrical connection between preferably separately housed hardware components, preferably using at least one independently connectable and releasable connector.

It is possible by means of such a connector unit to supply a corresponding control unit in a sterile operating area with voltage and/or to externally control it and/or to externally program it in that the described supply connection and/or the described data connection is/are established.

The control unit can then be supplied with voltage by means of the supply connection and the control unit can be externally controlled and/or programmed by means of the data connection.

Only one sterile cable connection is required here between the control interface of the connector unit and the integrated interface of the control unit, whereby the use in the sterile operating area is made possible in a simple and safe manner. Cable connections between the connector unit and the power supply and/or the data processing device as well as the power supply and/or the data processing device itself can be non-sterile and can be arranged outside the sterile operating area.

The connector unit and/or the connection cable can in particular be sterilizable, for instance sterilizable chemically and/or by irradiation and/or by the effect of pressure and/or temperature. The materials and/or processing (for example seals and/or packing) of the connector unit can be adapted to ensure the sterilizability.

The connector unit can be compact due to the common design of the supply and data connection and can thus enable a compact control system. The electrical safety is moreover increased and the handling improved due to the smaller number of connections.

Sterilizable components, for example the control unit and/or the connector unit and/or the connection cable may differ visually from non-sterilizable and thus always non-sterile components. The housing color and/or a corresponding print can be considered here, for example. The transition to the non-sterilizable or non-sterile components at the connector unit can be separately marked.

A control unit that is configured for use with the connector unit can furthermore be particularly compact, robust, simple to handle, and long-lasting since the data connection and the supply connection can be established solely by means of the integrated interface, that is no additional data interface or supply interface is required.

The connector unit can be configured to communicate with the control unit by means of the integrated interface and the control interface using a first communication protocol. The connector unit can be configured to communicate with the data processing unit by means of the data interface using a second communication protocol. The connector unit can be configured to convert communication data between the first and second communication protocols. The first and/or second communication protocol(s) can, for example, be a protocol from the group USB, UART, CAN, RS485, SPI, or another serial or parallel communication protocol.

A power pack and/or a socket and/or a rechargeable battery and/or a different kind of power supply can be provided as the power supply. A workstation computer, a portable terminal, or a different kind of data processing unit can be provided as the data processing unit to control and/or program the control unit.

The connector unit can have a rechargeable battery interface, for example a rechargeable battery slot, an internal rechargeable battery compartment, and/or a different kind of connection, in addition to the supply interface to connect the connector unit to a rechargeable battery. A supply connection of the control unit with the rechargeable battery can be established by means of the rechargeable battery interface. The user can choose in this case whether he, for instance, connects a power pack or a rechargeable battery to the connector unit that is or can be connected to the control unit.

The supply interface, the data interface, and the control interface are preferably wired electrical interfaces. An electrical interface by means of which a direct, electrically conductive contact can be established between two components is called wired here.

The connector unit can comprise a housing and at least one printed circuit board and/or integrated circuit. The connector unit can alternatively be formed as a Y cable without its own circuits, for example.

The supply interface can be configured to connect the connector unit to the power supply by means of a power supply connection cable. The data interface can be configured to connect the connector unit to the data processing unit by means of a data connection cable. The control interface can be configured to connect the connector unit to the control unit by means of a control connection cable. The connector unit can alternatively be configured for a direct plugging to the control unit (without an interposed connection cable) by means of a connector integrated in the connector unit.

The supply interface can have a connector to establish a releasable cable connection to the power supply, in particular by means of the power supply connection cable. The data interface can have a connector to establish a releasable cable connection to the data processing unit, in particular by means of the data connection cable. The control interface can have a connector to establish a releasable cable connection to the control unit, in particular by means of the control connection cable. The supply interface and/or the data interface and/or the control interface can be fixedly connected to a connection cable.

The connector unit can in particular comprise a connection cable, with the control interface being fixedly or releasably connectable or connected to a first end of the connection cable and with a second end of the connection cable having an integrated connector connectable to the integrated interface of the control unit to establish the supply connection and the power connection.

The connector unit can be watertight. The integrated connector of the connection cable can be connected to the integrated interface of the control unit in a watertight manner. A safe operation and a simple cleaning of the connector unit can thus be made possible.

The data interface can be or comprise a USB interface. The connector unit can comprise an interface controller circuit, in particular a USB controller circuit. A data interface for operation and/or for servicing and/or for controlling the control unit by medical staff can thus be provided even if the control unit itself does not comprise all the interface logics required for this purpose.

Providing additional interface logics in the control unit that are possibly required only during an operation and/or servicing and/or control of the control unit by medical staff, but not in regular operation on the patient, can thus also be avoided.

The connector unit can comprise, in particular in addition to a wired data interface, a wireless data interface, for example a Bluetooth interface, to establish a wireless data connection to a data processing unit. The connector unit can thus enable a particularly flexible control and/or programming of the control unit.

The connector unit can comprise an insulation barrier, in particular an air gap and/or a creepage distance for an electrical decoupling of the control unit from the data processing unit. The electrical safety of the connector unit and/or of the control system can be ensurable by the electrical decoupling by means of the insulation barrier. Provision can in particular be made that the insulation barrier satisfies the demands of a standard for the safety of medical devices, in particular the standard IEC 60601-1 in the version valid at the date of filing of the present application.

The proposed control unit to control an implantable blood pump comprises an integrated interface that is connectable to the control interface of a connector unit of the proposed kind to establish the supply connection and the data connection.

As explained above, the control unit configured in this manner for use with the connector unit can be compact, robust, and long-lasting and is suitable for operation in the sterile operating area.

The control unit can in particular be sterilizable for instance sterilizable chemically and/or by irradiation and/or by the effect of pressure and/or temperature. The materials and/or processing (for example seals and/or packing) of the control unit can be adapted to ensure the sterilizability.

The control unit can be configured for a single-part connection to at least one external rechargeable battery, i.e. for connection to the at least one external rechargeable battery without an interposed cable connection, in particular for a shape matched and/or force fit and/or watertight single-part connection, to the at least one external rechargeable battery. The control unit can be designed as particularly compact, robust, simple to handle, and long-lasting by the single-part connection to the at least one external rechargeable battery. The control unit can, for example, be configured for a simultaneous single-part connection to two external rechargeable batteries. The power supply can thus also be ensured on a failure/replacement of an external rechargeable battery.

Provision can be made that contacts arranged on the control unit for connection to the external rechargeable battery can be switched to deenergized and/or can be electrically insulated. The operational safety of the control unit in an operation without an external rechargeable battery (in particular in an operation with an internal rechargeable battery and/or with a power pack) can thus be improved.

The control unit can be an extracorporeal (that is not implantable) control unit. The control unit can be connectable to the blood pump to control the blood pump by means of a driveline that can comprise a reversibly connectable coupling. A putting into operation (for example during surgery to implant the blood pump) and/or a replacement and/or a servicing of the control unit can thereby be facilitated. The control unit can be connectable and/or connected to a TET module (transcutaneous energy transfer module) and/or to a transmission coil for wireless energy transmission. The blood pump can be controllable by means of the TET module and/or the transmission coil.

The control unit can have an internal rechargeable battery. The control unit can thus be operated at least temporarily when the external rechargeable battery or the external rechargeable batteries and/or an external power supply fail and/or are not available.

Provision can be made that the control unit does not have any further external wired electrical interface except for the following four external wired electrical interfaces the aforesaid integrated interface, a driveline interface to connect the control unit to the blood pump, a rechargeable battery interface to connect the control unit to an external rechargeable battery, and either a closable, preferably closable in a watertight manner, servicing interface to insert an internal rechargeable battery, or an additional rechargeable battery interface to connect the control unit to an additional external rechargeable battery. Provision can be made that the control unit has both the servicing interface and the additional rechargeable battery interface and does not have any further external wired electrical interface except for the thus indicated five external wired electrical interfaces.

The fact that such a minimal number of wired electrical interfaces is provided is particularly advantageous for the electrical safety and/or leak tightness (cf. IP protective classes for electrical operating means).

The proposed control system for an implantable blood pump comprises a connector unit of the proposed kind and a control unit of the proposed kind. Certain aspects and advantages of the control system result, for instance from the aforesaid aspects and advantages of the connector unit and control unit.

The control system can comprise a power supply unit that is selectively directly connectable or connectable by means of the connector unit to the integrated interface of the control unit. The power supply unit can thus, for instance, advantageously be connected by medical staff by means of the connector unit during operation and/or a servicing and/or control of the control unit so that a data connection can simultaneously be established, but is in contrast directly connected to the control unit in regular operation. The power supply unit can be configured for an on-grid operation of the control unit and/or to charge the external and/or internal rechargeable batteries. The power supply unit can itself be a rechargeable battery or can comprise a rechargeable battery.

The control unit of the control system can be sealed together with the connector unit of the control system in a sterile package. The control system can thus be providable and/or storable in a state that permits a fast and simple use, for instance in the sterile operating area during surgery for implanting the blood pump. The control unit can be sealed without the external rechargeable battery and/or the internal rechargeable battery in the sterile package for storage. Alternatively or additionally, the control unit and/or parts of the control unit, in particular the wired electrical interfaces of the control unit, can be covered or coverable by a sterile cover, for example a protective film. The corresponding parts of the control unit can thus be protected against liquids and/or contamination during surgery. The cover can be removed after the surgery.

BRIEF DESCRIPTION OF THE DRAWINGS

The aforesaid and further aspects and advantages of the proposed connector unit, the proposed control unit, and the proposed control system will be explained in more detail in the following with reference to drawings, FIG. 1 to FIG. 3. There are shown, schematically in each case.

DETAILED DESCRIPTION

Figure 1:
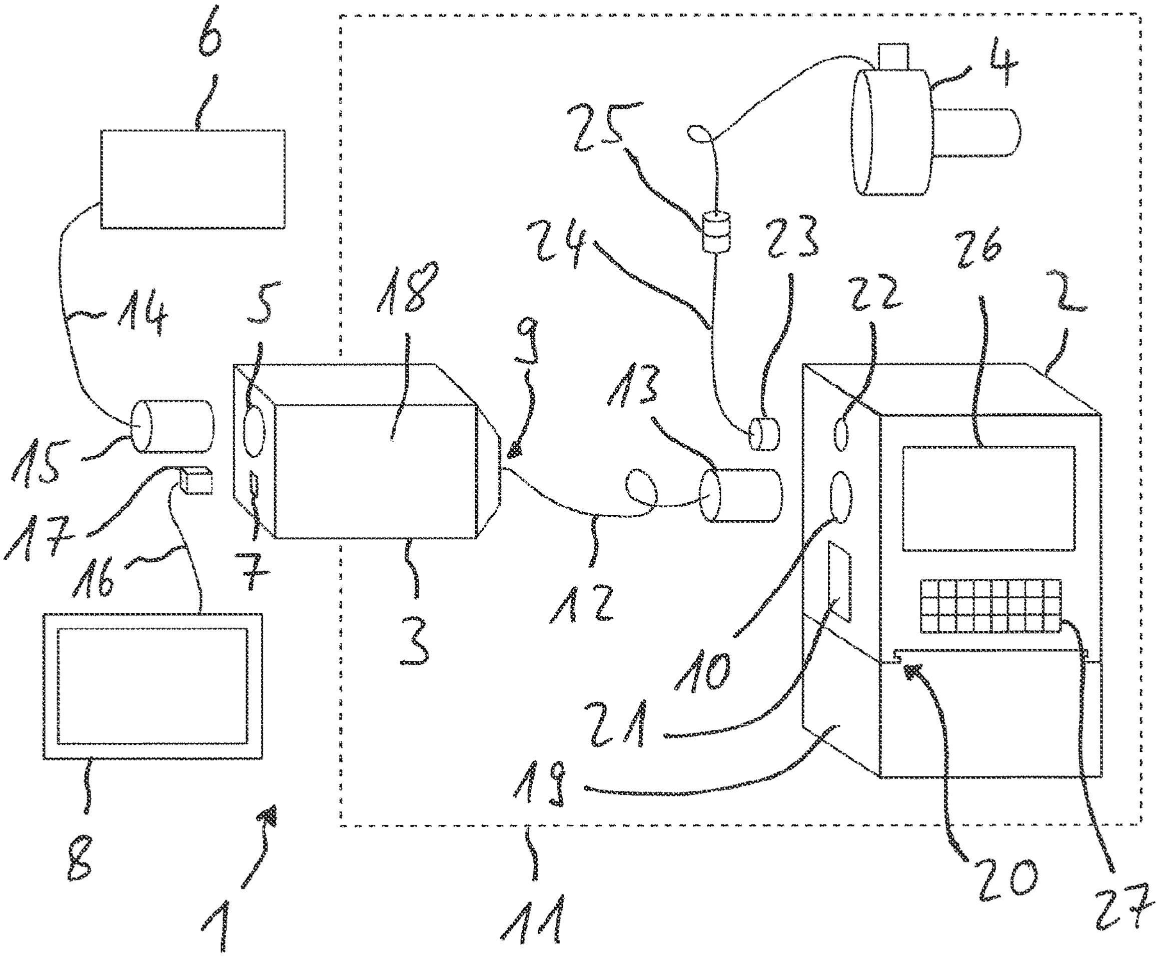
FIG. 1 is a control system for an implantable blood pump.

Repeating and similar features are provided with identical or similar alphanumeric reference numerals in the drawings. Reference numerals in a previously already explained drawing of shown features will be omitted in part in this respect. Furthermore, reference numerals already explained in connection with a previously explained drawing will not be explained again in part.

The control system 1 shown in FIG. 1 comprises a control unit 2 and a connector unit 3. The control unit 2 is configured to control an implantable blood pump 4 (the blood pump 4 itself is not necessarily a part of the control system 1).

The connector unit 3 comprises a supply interface 5 configured to connect the connector unit 4 to a power supply 6 and a data interface 7 configured to connect the connector unit 4 to a data processing unit 8.

The connector unit 3 further comprises a control interface 9 configured to connect the connector unit 3 to an integrated interface 10 of the control unit 2 so that a supply connection of the control unit 2 to the power supply 6 and a data connection 7 of the control unit 2 to the data processing unit 8 can simultaneously be established by means of the connector unit 3.

It is possible by means of the connector unit 3 to supply the control unit 2 in a sterile operating area 11 with voltage and/or to externally control it and/or to externally program it in that the supply connection and/or the described data connection is/are established. The control unit 2 can here be supplied with voltage by means of the supply connection and the control unit 2 can be externally controlled and/or programmed by means of the data connection.

The control interface 9 of the connector unit 3 is connectable to the integrated interface 10 of the control unit 2 by means of a first connection cable 12 (control connection cable) comprising a first connector 13 (integrated connector in which the function of a data connector and the function of a connection for the voltage supply are integrated).

The supply interface 5 is connectable to the power supply 6 by means of a second connection cable 14 (power supply connection cable) comprising a second connector 15. The data interface 7 is connectable to the data processing unit 8 by means of a third connection cable 16 (data connection cable) comprising a third connector 17.

In the configuration illustrated in FIG. 1, that is suitable for using the control unit 2 during surgery for the implantation of the blood pump 4, the control unit 2 and the first connection cable 12 are arranged in the sterile operating area 11. The power supply 6, the data processing unit 8, the second connection cable 14, and the third connection cable 16 are arranged outside the sterile operating area 11. The connector unit 13 is arranged at a transition to the sterile operating area 11 (for example at a sterile barrier).

The connector unit 3, the first connection cable 12 and the control unit 2 can be sterilizable, for instance sterilizable chemically and/or by irradiation and/or by the effect of pressure and/or temperature. The connector unit 3 can furthermore be watertight; the first connector 13 can be connectable to the integrated interface 10 of the control unit 2 in a watertight manner.

A power pack or a socket or a different kind of power supply can be provided as the power supply 6. A workstation computer, a portable terminal, or a different kind of data processing unit can be provided as the data processing unit 8 to control and/or program the control unit 2.

The supply interface 5, the data interface, 7 and the control interface 9 are wired electrical interfaces. The connector unit 3 comprises a housing 18 that includes a circuit board connected to the interfaces (in the interior of the housing 18). The connector unit 3 can alternatively be formed as a Y cable without a housing and/or its own circuits, for example. The data interface 7 and/or the control interface 9 can alternatively or additionally comprise wireless interface components.

The supply interface 5 has a connector for establishing a releasable cable connection to the power supply. The data interface 7 has a connector for establishing a releasable cable connection to the data processing unit 8. The supply interface 5 and/or the data interface 7 can alternatively be fixedly connected to the respective connection cable 14, 16.

The control interface 9 is fixedly connected to the first connection cable 12. The control interface 9 can alternatively have a connector for establishing a releasable cable connection to the control unit 2.

The control system 1 further comprises an external rechargeable battery 19. The control unit 2 is configured for the single-part connection to the external rechargeable battery 19 by means of a rechargeable battery interface 28, i.e. for a connection to the external rechargeable battery 19 without an interposed cable connection. The external rechargeable battery 19 is configured with the control unit 2 for the shape matched, force fit (by latching) and watertight single-part connection to the control unit 2 by means of a latchable insertion rail 20. The external rechargeable battery 19 can alternatively be connectable to the control unit 2 by means of a cable connection.

The control unit 2 comprises a servicing interface 21 for the insertion of an internal rechargeable battery. The servicing interface 21 is preferably closable, particularly preferably closable in a watertight manner.

The control unit 2 is an extracorporeal (that is not implantable) control unit. The control unit 2 comprises a driveline interface 22. The driveline interface 22 is connectable to the blood pump 4 by means of a driveline 24 (having a fourth connector 23) for controlling the blood pump 4. The driveline 24 comprises a reversibly connectable coupling 25. The driveline 24 can alternatively be designed as a single part, that is without a coupling.

The control unit 2 comprises a display 26 for displaying operating parameters and/or control options of the control unit 2 and/or of the blood pump 4 as well as a control panel 27 for controlling the control unit 2. The control panel 27 can, for example, be a keypad or a touch panel. The control panel 27 can also be integrated in the display 26, for example in conjunction with a touchscreen on the display 26. The display 26 and/or the control panel 27 can also be omitted. In this case, the control unit 2 can, for example, be connectable to an external display and/or to an external operating unit.

The control unit 2 does not comprise any further external wired electrical interface except for the following four external wired electrical interfaces: the integrated interface 10, the driveline interface 22, the rechargeable battery interface 28, and the servicing interface 21. The control unit 2 can alternatively comprise at least one further wired electrical interface, for example an additional data interface (for instance for a connection to an external display and/or to an external operating unit).

The power supply 6 is a power supply unit that is selectively directly connectable or connectable to the integrated interface of the control unit 2 by means of the connector unit 3. The second connector 15 is selectively connectable to the connector of the supply interface 5 of the connector unit 3 or to the integrated interface 10 of the control unit 2 for this purpose. The power supply unit can be configured for a wired operation of the control unit 2 and/or for charging the external rechargeable battery 19 and/or the internal rechargeable battery.

The second connector 15 can alternatively only be connectable to the supply interface 5, but not to the integrated interface 10. In this case, a standalone power supply unit can be provided for a direct voltage supply of the control unit 2 (without any connector unit 3).

The data interface 7 is a USB interface, but can also be a different kind of data interface. The connector unit 3 comprises an interface controller circuit, in this example a USB controller circuit. The interface controller circuit can alternatively be a part of the control unit 2; provision can then be made that the connector unit 3 does not comprise its own interface logic.

The connector unit 3 has a wireless data interface, preferably a Bluetooth interface, in addition to the wired data interface 7. Additionally, or alternatively to the wired data connection, a wireless data connection of the control unit 2 to the data processing unit 8 can be established by means of said Bluetooth interface without the control unit 2 itself comprising a wireless data interface. The wireless data interface can alternatively be omitted. The control unit 2 can also alternatively comprise a wireless data interface.

The control unit 2 of the control system 1 can be sealed in a sterile package together with the connector unit of the control system so that the control system 1 can be provided and stored in a state that enables a fast and simple use, for instance in the sterile operating area 11. Provision is made here that the control unit 2 is sealed without the external rechargeable battery 19 and the internal rechargeable battery in the sterile package.

Figure 2:
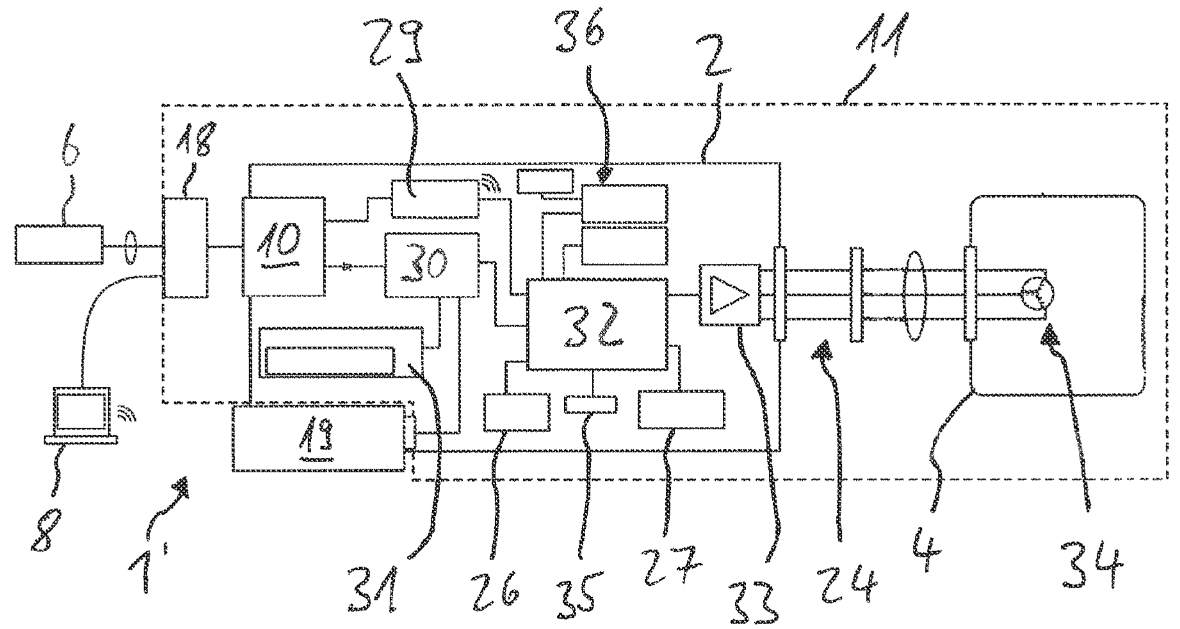
FIG. 2 is a block diagram of the control system in accordance with a further example.

The control system 1' shown in FIG. 2 is largely similar to the control system 1 shown in FIG. 1 so that only differences and additionally shown details (that can also be provided in control system 1 or 1") are described, with these differences and details showing optional features of a control system of the proposed kind. FIG. 2 in particular illustrates the architecture of an exemplary control unit 2.

In the example of the control system 1', the control unit 2 comprises an interface controller circuit 29. The interface controller circuit 29 comprises a UART controller circuit for establishing the wired data connection and a Bluetooth controller circuit for establishing a wireless data connection to the data processing unit 8. The connector unit 3 in this case comprises a USB controller circuit and is configured to convert communication data between a USB communication protocol for communication with the data processing unit 8 and a UART communication protocol for communication with the control interface 2. The use of different communication protocols, for example CAN, RS485, SPI, etc. can also be provided.

The control unit 2 of the control system 1' comprises a main controller 32 configured to control different components of the control unit 2 as well as a motor control 33 configured to control a pump motor 34 of the blood pump 4.

The control unit 2 further comprises a power management circuit 30 configured to control a voltage supply of the main controller 32, the blood pump 4, and other components of the control system 1. The power management circuit 30 is further configured to control a charging and/or discharging of the internal rechargeable battery 31 and of the external rechargeable battery 19.

The control unit 2 further comprises an expansion interface 35 by means of which the control unit 2 is connectable to an expansion unit. The expansion unit can, for example, be a memory expansion, in particular a memory card. The expansion interface 35 is preferably closable, in particular closable in a watertight manner. The expansion interface 35 can, for example, be arranged within the servicing interface for receiving the internal rechargeable battery 31 so that the expansion interface 35 is closable together with the servicing interface.

The control unit can optionally comprise further components 36, for example one or more sensors (for sensing an operating state of the control unit 2 and/or of the blood pump 4) and/or alarms (for outputting a message on an operating state of the control unit 2 and/or of the blood pump 4).

Figure 3:
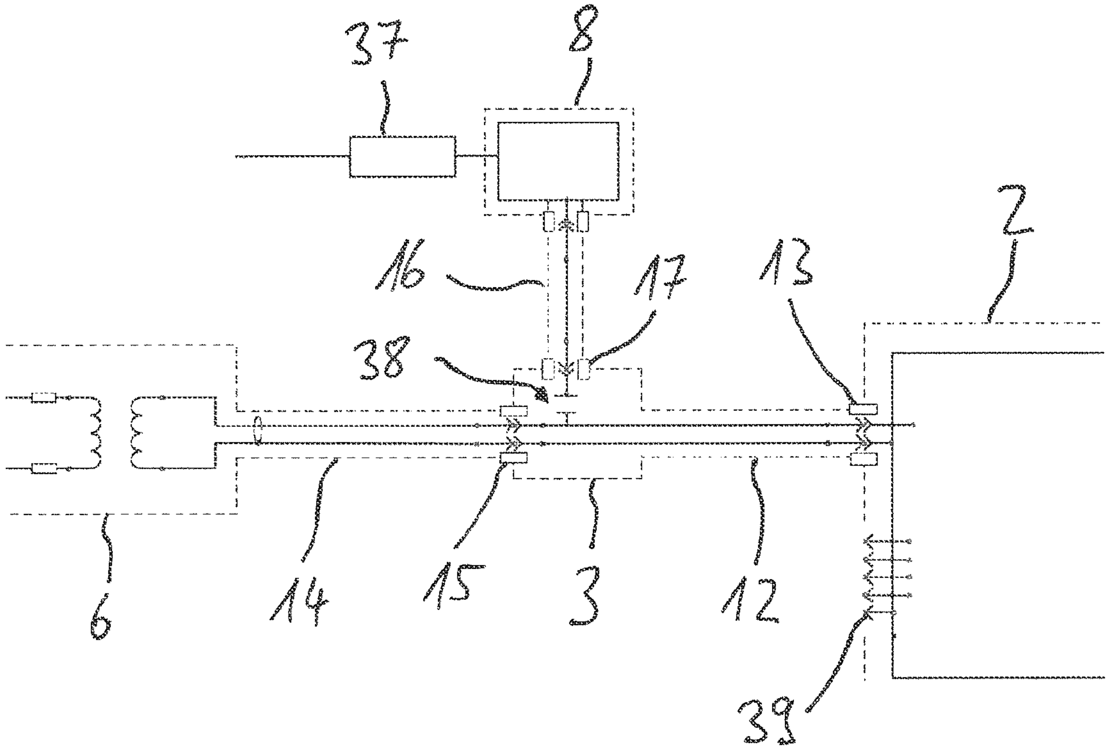
FIG. 3 is a circuit diagram of a part of the control system in accordance with a further example.

The control system 1" shown in part in FIG. 3 is largely similar to the control system 1 shown in FIG. 1 so that only differences and additionally shown details (that can also be provided in control system 1 or 1") are looked at, with these differences and details showing optional features of a control system of the proposed kind. FIG. 3 in particular illustrates aspects of the control system 1" that serve electrical safety.

The connector unit 3 of the control system 1" comprises an insulation barrier 38 implemented as an air gap and/or a creepage distance between conductor elements on a circuit board of the connector unit 3. The insulation barrier is configured for the electrical decoupling of the control unit 2 from the data processing unit 8, in particular from a power pack 27 or from another voltage supply of the data processing unit 8. Provision is preferably made that the insulation barrier satisfies the demands of the standard IEC 60601-1 in the version applicable on the date of the current application (or another standard for the safety of medical devices).

Contacts 39 arranged on the control unit 2 for connection to the external rechargeable battery are electrically insulatable and thus switchable to deenergized. The control unit 2 is configured to automatically switch the contacts 39 to deenergized on the removal of the external rechargeable battery.

The disclosure further relates to the following aspects:

1. A connector unit (3) for a control unit (2) configured to control an implantable blood pump (4), wherein the connector unit (3) comprises:
   a supply interface (5) configured to connect the connector unit (3) to a power supply (6);
   a data interface (7) configured to connect the connector unit (3) to a data processing unit (8); and a control interface (9) configured to connect the connector unit (3) to an integrated interface (10) of the control unit (2) so that a supply connection of the control unit (2) to the power supply (6) and a data connection of the control unit (2) to the data processing unit (8) can simultaneously be established by means of the connector unit (3).
2. A connector unit (3) in accordance with aspect 1 further comprising a connection cable (12), wherein the control interface (9) is fixedly or releasably connectable or connected to a first end of the connection cable (12); and wherein a second end of the connection cable (12) has an integrated connector (13) connectable to the integrated interface (10) of the control unit (2) to establish the supply connection and the power connection.
3. A connector unit (3) in accordance with aspect 2, wherein the integrated connector (13) of the connection cable (12) is connectable to the integrated interface (10) of the control unit (2) in a watertight manner.
4. A connector unit (3) in accordance with one of the preceding aspects, wherein the connector unit (3) is sterilizable and/or the connection cable (12) is sterilizable.
5. A connector unit (3) in accordance with one of the preceding aspects, wherein the connector unit (3) comprises a USB controller circuit (29) and the data interface (7) is or comprises a USB interface.
6. A connector unit (3) in accordance with one of the preceding aspects, wherein the connector unit (3) comprises an insulation barrier (38), in particular an air gap and/or a creepage distance, for an electrical decoupling of the control unit (2) from the data processing unit (8).
7. A control unit (2) to control an implantable blood pump (4) comprising an integrated interface (10) that is connectable to the control interface (9) of a connector unit (3) in accordance with one of the aspects 1 to 6 to establish the supply connection and the data connection.
8. A control unit (2) in accordance with aspect 7 configured for a single-part connection to at least one rechargeable battery (19), i.e. for connection to the at least one external rechargeable battery (19) without an interposed cable connection, in particular for a shape matched and/or force fit and/or watertight single-part connection, to the at least one external rechargeable battery (19).
9. A control unit (2) in accordance with aspect 8, wherein contacts (39) arranged on the control unit (2) for connection to the external rechargeable battery (19) can be switched to deenergized and/or can be electrically insulated.
10. A control unit (2) in accordance with one of the aspects 7 to 9, wherein the control unit (2) is sterilizable.
11. A control unit (2) in accordance with one of the aspects 7 to 10, wherein the control unit (2) is an extracorporeal control unit (2) and is connectable to the blood pump (4) to control the blood pump (4) by means of a driveline (24) that comprises a reversibly connectable coupling (25).
12. A control unit (2) in accordance with one of the aspects 7 to 11, wherein the control unit (2) does not have any further external wired electrical interface except for the following four external wired electrical interfaces the aforesaid integrated interface (10), a driveline interface (22) to connect the control unit (2) to the blood pump (4), a rechargeable battery interface (28) to connect the control unit (2) to an external rechargeable battery (19), and either a closable, preferably closable in a watertight manner, servicing interface (21) to insert an internal rechargeable battery (31), or an additional rechargeable battery interface to connect the control unit (2) to an additional external rechargeable battery.
13. A control system for an implantable blood pump (4) comprising:
   a connector unit (3) in accordance with one of the aspects 1 to 6; and a control unit (2) in accordance with one of the claims 7 to 12.

14. A control system in accordance with aspect 13 further comprising a power supply unit (6) that is selectively directly connectable or connectable by means of the connector unit (3) to the integrated interface (10) of the control unit (2).

15. A control system in accordance with aspect 13 or aspect 14, wherein the control unit (2) is sealed in a sterile package together with the connector unit (3).

LIST OF REFERENCE NUMERALS

1, 1', 1" control system
2 control unit
3 connector unit
4 blood pump
5 supply interface
6 power supply
7 data interface
8 data processing unit
9 control interface
10 integrated interface
11 sterile operating area
12 first connection cable
13 first connector
14 second connection cable
15 second connector
16 third connection cable
17 third connector
18 housing
19 external rechargeable battery
20 insertion rail
21 servicing interface
22 driveline interface
23 fourth connector
24 driveline
25 coupling
26 display
27 control panel
28 rechargeable battery interface
29 interface controller circuit
30 power management circuit
31 internal rechargeable battery
32 main controller
33 motor control
34 pump motor
35 expansion interface
36 further components
37 power pack
38 insulation barrier
39 contacts

The invention claimed is:

1. A connector unit for a control unit, the control unit configured to control an implantable blood pump, wherein the connector unit comprises:

a supply interface configured to connect the connector unit to a power supply;

a data interface configured to connect the connector unit to a data processing unit; and a control interface configured to connect the connector unit to an integrated interface of the control unit so that a supply connection of the control unit to the power supply and a data connection of the control unit to the data processing unit can simultaneously be established by the connector unit;

wherein the connector unit comprises a USB controller circuit and the data interface comprises a USB interface;

wherein the connector unit comprises an insulation barrier for an electrical decoupling of the control unit from the data processing unit.

2. A connector unit in accordance with claim 1, further comprising:

a control connection cable, wherein the control interface is fixedly or releasably connectable to a first end of the control connection cable, wherein a second end of the control connection cable has an integrated connector connectable to the integrated interface of the control unit to establish the supply connection and the power connection.

3. A connector unit in accordance with claim 2, wherein the integrated connector of the control connection cable is connectable to the integrated interface of the control unit in a watertight manner.

4. A connector unit in accordance with claim 1, wherein the connector unit or the control connection cable is sterilizable.

5. A connector unit in accordance with claim 1, wherein the supply interface is configured to connect the connector unit to the power supply by a power supply connection cable and the data interface is configured to connect the connector unit to the data processing unit by a data connection cable.

6. A connector unit in accordance with claim 1, further comprising:

a rechargeable battery interface to connect the connector unit to a rechargeable battery so that a supply connection of the control unit to the rechargeable battery can be established.

7. A connector unit in accordance with claim 1, wherein the insulation barrier comprises an air gap.

8. A connector unit in accordance with claim 1, wherein the insulation barrier comprises a creepage distance.

9. A control system for an implantable blood pump comprising:

a connector unit that comprises:

a supply interface configured to connect the connector unit to a power supply;

a data interface configured to connect the connector unit to a data processing unit; and a control interface configured to connect the connector unit to an integrated interface of the control unit so that a supply connection of the control unit to the power supply and a data connection of the control unit to the data processing unit can simultaneously be established by the connector unit; and a control unit that comprises:

an integrated interface that is connectable to the control interface of the connector unit to establish the supply connection and the data connection;

wherein the connector unit comprises a USB controller circuit and the data interface comprises a USB interface;

wherein the connector unit comprises an insulation barrier for an electrical decoupling of the control unit from the data processing unit.

10. A control system in accordance with claim 9, further comprising:

a power supply unit that is connectable by the connector unit to the integrated interface of the control unit.

11. A control system in accordance with claim 9, wherein the control unit is sealed in a sterile package with the connector unit.

12. A control system in accordance with claim 9, wherein the insulation barrier comprises an air gap.

13. A control system in accordance with claim 9, wherein the insulation barrier comprises a creepage distance.

* * * * *